(12) United States Patent
Carroll et al.

(10) Patent No.: US 7,935,820 B2
(45) Date of Patent: May 3, 2011

(54) METHODS FOR N-DEMETHYLATION OF MORPHINE AND TROPANE ALKALOIDS

(75) Inventors: Robert James Carroll, St. Catharines (CA); Hannes Leisch, St. Catharines (CA); Tomas Hudlicky, St. Catharines (CA)

(73) Assignee: Brock University, St. Catharines (CA)

( * ) Notice: Subject to any disclaimer, the term of this patent is extended or adjusted under 35 U.S.C. 154(b) by 828 days.

(21) Appl. No.: 11/771,227

(22) Filed: Jun. 29, 2007

(65) Prior Publication Data

US 2009/0005564 A1  Jan. 1, 2009

(51) Int. Cl.
*C07D 489/02* (2006.01)
*C07D 489/08* (2006.01)

(52) U.S. Cl. ........................................ 546/45; 546/46

(58) Field of Classification Search ............... 546/45, 546/46
See application file for complete search history.

(56) References Cited

U.S. PATENT DOCUMENTS 7,405,301 B2 * 7/2008 Scammells et al. ............. 546/44

OTHER PUBLICATIONS

Ripper, "*Photochemical N-Demethylation of Alkalodis*", Bioorg. Med. Chem. Lett. 11 (2001) 443-445.

* cited by examiner

*Primary Examiner* — Charanjit S Aulakh
(74) *Attorney, Agent, or Firm* — Occhiuti Rohlicek & Tsao LLP

(57) ABSTRACT

The present invention provides a method for the N-demethylation of an N-methylated heterocycle, particularly a morphine or tropane alkaloid or derivative thereof. The method comprises reacting the heterocycle with a metal catalyst and a solvent in the presence of an oxidizing agent.

32 Claims, No Drawings

METHODS FOR N-DEMETHYLATION OF MORPHINE AND TROPANE ALKALOIDS

FIELD OF THE INVENTION

The present invention relates to N-methylated compounds and methods for N-demethylation of same. In particular the present invention relates to morphine and tropane alkaloids and their derivatives and methods for N-demethylation of same.

BACKGROUND OF THE INVENTION

The semisynthesis of morphine-derived antagonists, such as naloxone, see compound 5 below, and naltrexone see compound 6 below, and other medicinally significant compounds, from opium-derived natural products traditionally involves standard procedures for demethylation followed by subsequent procedures such as oxidative procedures for the introduction of a C-14 hydroxyl group.

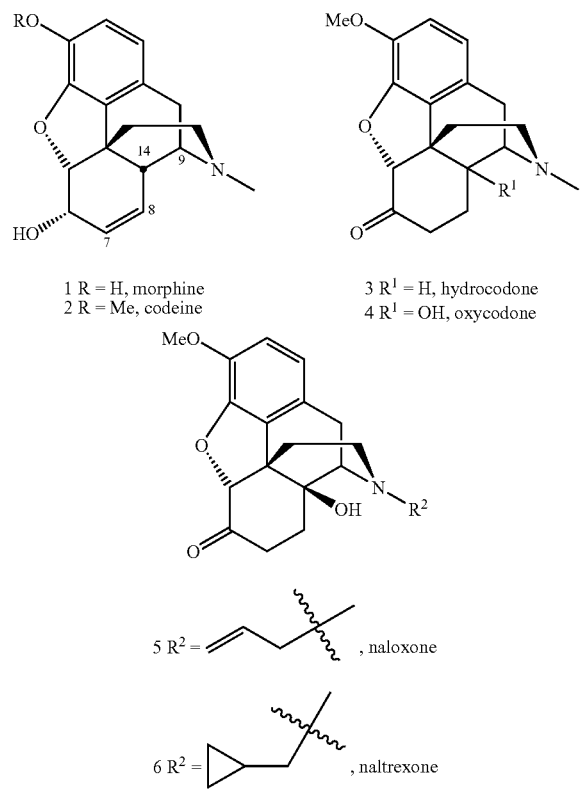

1 R = H, morphine
2 R = Me, codeine
3 $R^1$ = H, hydrocodone
4 $R^1$ = OH, oxycodone 5 $R^2$ = , naloxone 6 $R^2$ = , naltrexone Most commercial procedures for the production of C-14 hydroxylated species take advantage of $\Delta_{7\text{-}8}$ unsaturated species, however compounds containing α, β-unsaturated ketones have recently been identified as potential genotoxins because of their Michael acceptor character, and therefore routes to the oxygenated derivatives must avoid these intermediates.

Therefore any method that avoids these standard procedures may hold immense commercial potential for the production of morphine-derived antagonists, such as naloxone 5, naltrexone 6, and other medicinally significant compounds.

The development of a mild catalytic protocol for N-demethylation of ring-C saturated morphinans would simplify strategies toward C-14 oxygenated derivatives via potential use of an intramolecular process by tethered functionalisation anchored at the nitrogen atom.

N-Demethylation of morphine-type alkaloids has been extensively studied. The standard procedures for N-demethylation of substrates including morphinan derived compounds include the use of cyanogen bromide (the von Braun reaction)[1], the reaction of a tertiary amine with chloroformates followed by hydrolysis[2], as well as a photochemical demethylation procedure[3]. Other methods that have been used to effect demethylation include amongst others, Polonovski-type reactions[4]. Precedent for a Pd-catalyzed oxidative demethylation procedure using stoichiometric amounts of Pd/C, appears in a single report by Chaudhuri[5].

Chaudhuri's method describes the use of Pd/C (1 g/1 g substrate) in MeOH at room temperature to dealkylate tertiary amines. On occasion he notes that small amounts of N-formyl species were isolated. This was an undesired side reaction for his methodology. Application of the conditions described in this paper to hydrocodone results in no N-demethylation. The only product recovered was N-formyl hydrocodone. Thus, there remained a need for a truly practical method for the production of demethylated morphine derivatives.

SUMMARY OF THE INVENTION

An investigation of the chemistry of morphine alkaloids and their derivatives, such as hydrocodone 3, and oxycodone 4, led to the present invention, which involves a method for a one-pot oxidative N-demethylation.

In one aspect the present invention provides a one-pot method for N-demethylation of N-methylated compounds.

The present invention provides a one-pot method for the N-demethylation of an N-methylated heterocycle comprising mixing the N-methylated heterocycle with a metal catalyst in the presence of an oxidizing agent.

In a preferred embodiment, the N-methylated heterocycle is selected from the group consisting of a morphine alkaloid, a tropane alkaloid and derivatives thereof. The morphine alkaloid is selected from the group below: thebaine, oripavine, 14-hydroxycodeinone, 14-hydroxymorphinone, morphine, codeine, hydromorphone, hydrocodone, oxymorphone, oxycodone, hydromorphol and oxymorphol. A preferred morphine alkaloid is hydrocodone. The tropane alkaloid is preferably selected from the group consisting of tropinone, tropane, tropine, atropine, cocaine or any other bicyclo-[3.2.1]-azabicyclic methylamines.

In one embodiment of the invention the metal catalyst can also act as the oxidizing agent.

In another embodiment of the invention the oxidizing agent is selected from the group consisting of oxygen, ammonium persulfate, hydrogen peroxide, m-CPBA, peracetic acid, magnesium mono peroxyphthalate; palladium, palladium acetate and combinations thereof. In a further preferred embodiment, the oxidizing agent is palladium acetate or ammonium persulfate.

In a preferred embodiment of the invention, the catalyst is selected from the group consisting of: CuCl, CuI, CuOAc$_2$, CuCO$_3$, CUSO$_4$, CuCl$_2$, CuO, Pd(OAc)$_2$, PdCl$_2$, PdCl$_2$(PPh$_3$)$_4$, PdBr$_2$, Pd(acac)$_2$, Pd$_2$(dba)$_3$, Pd(dba)$_2$, Pd(PPh$_3$)$_4$, Fe dust, Cu, Fe, Ru, Ir, Ni, Pd, Pt, Ge, Sn, Os, Ag, Au, Pb.

In another preferred embodiment, the catalyst is a copper catalyst selected from the group consisting of Cu, CuCl, CuI, Cu(OAc)$_2$, CuCO$_3$, CuSO$_4$, CuCl$_2$, and CuO. In a further preferred embodiment the catalyst is Cu(OAc)$_2$.

In yet another embodiment the preferred catalyst is selected from the group consisting of Pd(OAc)$_2$, PdCl$_2$, PdCl$_2$(PPh$_3$)$_4$, PdBr$_2$, Pd(acac)$_2$, Pd$_2$(dba)$_3$, Pd(dba)$_2$, Pd(PPh$_3$)$_4$, most preferably Pd(OAc)$_2$.

The catalyst is preferably present in the range of from about 0.1 equivalents to about 5.0 equivalents, more preferably in the range of from about 1.0 equivalents to 2.5 equivalents, most preferably in about 2.5 equivalents.

In a preferred embodiment the catalyst is present in the range of from about 1.0 equivalents to 2.5 equivalents and the oxidizing agent is present in the range of 2.0 equivalents to 4.0 equivalents.

In a further preferred embodiment the catalyst is a copper salt and the oxidizing agent is ammonium persulfate.

In another aspect at least one solvent is added to the reaction mixture. The solvent is selected from the group consisting of water, benzene, dioxane, toluene, acetonitrile, C1 to C4 alcohols and mixtures thereof. One preferred solvent is acetonitrile:water in a ratio of about 5:1.

In another aspect of the invention, demethylated products obtained by the method of the invention are also encompassed within the invention.

The development of a Pd or Cu catalyst mediated demethylation method for the N-demethylation of morphinan alkaloids provides a very practical way to obtain normorphine products.

DETAILED DESCRIPTION

The present invention provides a one-pot method for catalysed N-demethylation of N-methylated heterocycles. The method is particularly useful for the demethylation morphine alkaloids or tropane alkaloids to provide highly desired products. The method of the invention is highly reproducible and efficient.

Briefly, the method comprises reacting an alkaloid substrate with a metal catalyst in the presence of an oxidizing agent. In some cases, the metal itself can act as an oxidizing agent. Atmospheric oxygen can also act as an oxidizing agent. In other cases, an additional oxidizing agent is added.

Various types of alkaloids such as oripavine, morphine, codeine, hydromorphone, hydrocodone, oxymorphone, oxycodone, tropinone, tropane, tropine, atropine, cocaine, and bicyclo-[3.2.1]-azabicyclic methylamines can be demethylated using the methods of the invention.

While a preferred morphine alkaloid derivative is hydrocodone and the examples focus on the demethylation of hydrocodone, it is apparent that other alkaloids can also be demethylated by the present methods.

Various types of catalyst can be used to obtain demethylated products. Palladium-based catalyst such as PdCl$_2$, Pd(OAc)$_2$, Pd(PPh$_3$)$_4$ and Pd(dba)$_2$ have been shown to be particularly useful. Pd(OAc)$_2$ in particular, results in significant yields of product.

Copper based catalysts have also been shown to be excellent catalysts for use in the method. A particularly effective catalyst is Cu(OAc)$_2$.

Under certain conditions, it is desirable to include a solvent. The solvent is typically water, benzene, dioxane, toluene, acetonitrile, C$_1$ to C$_4$ alcohols or a mixture of any of these.

Without being limiting, the following conditions are usually used:
(a) The substrate is dissolved in a solvent;
(b) A catalyst is added;
(c) An oxidant is added;
(d) The reaction proceeds from about 8 to 40 hours, optionally at room temperature, optionally at an elevated temperature;
(e) The solvent is removed;
(f) The residue is resuspended in an aqueous basic medium;
(g) The aqueous phase is extracted, dried and filtered, and
(h) Any remaining volatiles are removed.

While the basic steps of the methods remain constant, the optimal conditions for demethylation vary, depending upon the starting substrate, the catalyst used, the solvent used, the length of the reaction and temperature of the reaction. As discussed above, various types of substrate, catalyst and oxidants can be used. Reaction times typically vary from about 8 to 40 hours depending on the catalyst and temperature. Demethylated compounds have been recovered at reaction temperatures ranging from room temperature to about 90'. For example, when palladium acetate is used as a catalyst for the demethylation of hydrocodone in the presence of benzene, optimal yield is achieved when the reaction is heated to about 80' and the reaction proceeds for 36 hours. On the other hand, the combination of Cu(OAc)$_2$ as a catalyst with (NH$_4$)$_2$S$_2$O$_8$ as the oxidizing agent was shown to be highly efficient after a reaction time of 9 hours at room temperature. The relative amounts of the substrate, the catalyst and the oxidant also affects the yield.

Concentrations of about 0.01-100 mL solvent/gram of alkaloid is typically used in a small scale reaction.

The amount of catalyst is typically in the range of about 1 equivalent to 4 equivalents, more preferably about 2.0 equivalents to 2.5 equivalents, most preferably about 2.5 equivalents.

Dioxane, benzene and acetonitrile are preferred solvents. In particular a ratio of about 5:1 acetonitrile to water is effective.

A few exemplary procedures are shown in the Examples below. Although these examples focus on the demethylation of hydrocodone and codeine, it is apparent that the general chemistry can be applied to other morphine and tropane alkaloids and that other catalysts and oxidants that function in a similar manner to those used in the specific examples are also useful in the invention.

The above disclosure generally describes the present invention. It is believed that one of ordinary skill in the art can, using the preceding description, make and use the compositions and practice the methods of the present invention. A more complete understanding can be obtained by reference to the following specific examples. These examples are described solely to illustrate preferred embodiments of the present invention and are not intended to limit the scope of the invention. Changes in form and substitution of equivalents are contemplated as circumstances may suggest or render expedient. Other generic configurations will be apparent to one skilled in the art. All journal articles and other documents such as patents or patent applications referred to herein are hereby incorporated by reference.

EXAMPLES

Although specific terms have been used in these examples, such terms are intended in a descriptive sense and not for purposes of limitation. Methods of molecular biology, biochemistry and chemistry referred to but not explicitly described in the disclosure and these examples are reported in the scientific literature and are well known to those skilled in the art.

Example 1

General Procedure for Demethylation Using Palladium Acetate

Tertiary amine (0.1 mmol, 1.0 eq.) was dissolved in benzene (1 ml) and Pd(OAc)$_2$ (0.25 mmol, 2.5 eq.) added. The reaction was heated at reflux for 36 hours, cooled to room temperature and passed through a plug of silica using $CHCl_3$:$MeOH$:$NH_4OH$ 80:20:1 as eluent. The volatiles were removed in-vacuo, and the residue suspended in a saturated aqueous solution of $NaHCO_3$. The aqueous phase was extracted with $CHCl_3$, dried over magnesium sulphate, filtered and the volatiles removed in-vacuo. Column chromatography (silica gel; $CHCl_3$:$MeOH$:$NH_4OH$ 96:4:1) of the crude material affords analytically pure demethylated product.

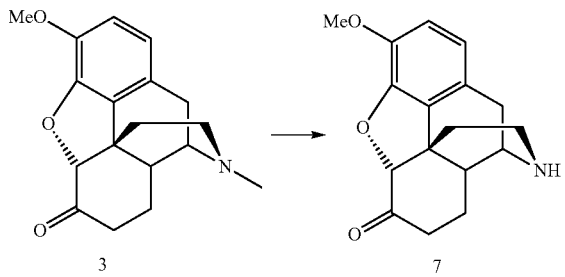

TABLE 1

N-demethylation of hydrocodone bitartrate 3

| Entry | Conditions (15 hrs, unless otherwise noted) | yield of 7 (%) |
|---|---|---|
| 1 | $Pd(OAc)_2$ (1.2 equiv.), benzene, 80° C. | 20% (70% rec. SM) |
| 2 | $Pd(OAc)_2$ (2.5 equiv.), benzene, 80° C. 36 hrs | 40% (55% rec. SM) |

Example 2

General Procedure for Demethylation Using Copper(II) Acetate

Tertiary amine (0.1 mmol, 1.0 eq.) was dissolved in $CH_3CN$:$H_2O$; 5:1 and $Cu(OAc)_2$ (0.2 mmol, 2.0 eq.) and $(NH_4)_2S_2O_8$ (0.4 mmol, 4.0 eq.) were added. The reaction was stirred at room temperature for 12 hours. The reaction mixture was quenched by the addition of aqueous 10% $Na_2S_2O_3$ solution. The organic solvent was removed in-vacuo, and the residue was basified to pH 9 using concentrated aqueous $NH_4OH$. The aqueous phase was extracted with DCM, dried over magnesium sulphate, filtered and the volatiles were removed in-vacuo. Column chromatography (silica gel; $CHCl_3$:$MeOH$:$NH_4OH$ 96:4:1) of the crude material affords analytically pure demethylated product.

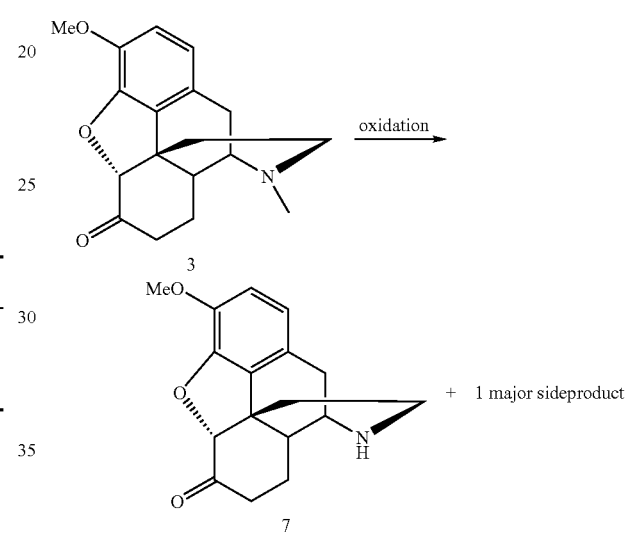

| Entry | Catalyst | Oxidant | Conditions | Norhydrocodone (7) | Side-product | Hydrocodone |
|---|---|---|---|---|---|---|
| 1 | $Cu(OAc)_2$ 0.5 eq. | $(NH_4)_2S_2O_8$ 2 eq. | 20% AcOH, rt (4 hrs) -> 80° C. (16 hrs) | various side products | | 75% |
| 2 | $Cu(OAc)_2$ 0.5 eq. | $(NH_4)_2S_2O_8$ 2 eq. | $CH_3CN$/$H_2O$; 5:1; rt | 20% | 8% | 64% |

Variation of Catalyst and Oxidant Loading:

All reactions were carried out at room temperature and under an atmosphere of air, utilising $CH_3CN$:$H_2O$ 5:1 as solvent and 9 hours reaction time.

| Entry | $Cu(OAc)_2$ | $(NH_4)_2S_2O_8$ | Norhydrocodone (7) | Side product | Hydrocodone |
|---|---|---|---|---|---|
| 1 | 0.5 eq. | 2 eq. | 20% | 8% | 64% |
| 2 | 1 eq. | 2 eq. | 36% | 7% | 46% |
| 3 | 2 eq. | 4 eq. | 64% | 20% | 10% |
| 4 | 1 eq. | 4 eq. | 36% | 12% | 38% |
| 5 | 0.5 eq. | 4 eq. | 24% | 7% | 55% |

Reaction temperature 50° C.

| Entry | Cu(OAc)$_2$ | (NH$_4$)$_2$S$_2$O$_8$ | Norhydrocodone (7) | Side product | Hydrocodone |
|---|---|---|---|---|---|
| 1 | 0.5 eq. | 2 eq. | 42% | 10% | 32% |

Various Atmospheres

Reaction conditions: 2 eq. Cu(OAc)$_2$, 4 eq. (NH$_4$)$_2$S$_2$O$_8$, CH$_3$CN:H$_2$O; 5:1, RT, 16 hrs

| Entry | Atmosphere | Norhydrocodone (7) | Side product | Hydrocodone |
|---|---|---|---|---|
| 1 | Oxygen | 53% | 23% | 15% |
| 2 | Argon | 50% | 18% | 18% |

Solvent Screening

Reaction conditions: 2 eq. Cu(OAc)$_2$, 4 eq. (NH$_4$)$_4$S$_2$O$_8$, RT, 16 hrs.

| Entry | Solvent | Norhydrocodone | Side product | Hydrocodone |
|---|---|---|---|---|
| 1 | CH$_3$CN:H$_2$O 5:1 | 64% | 20% | 10% |
| 2 | CH$_3$CN | 30% | Traces | 56% |
| 3 | CH$_3$CN:H$_2$O 1:1 | 45% | 34% | 18% |

Example 3

Demethylation of Codeine

Codeine was demethylated using following conditions: 2 eq. Cu(OAc)$_2$, 4 eq. (NH$_4$)$_2$S$_2$O$_8$, CH$_3$CN:H$_2$O; 5:1, RT, 16 hrs.

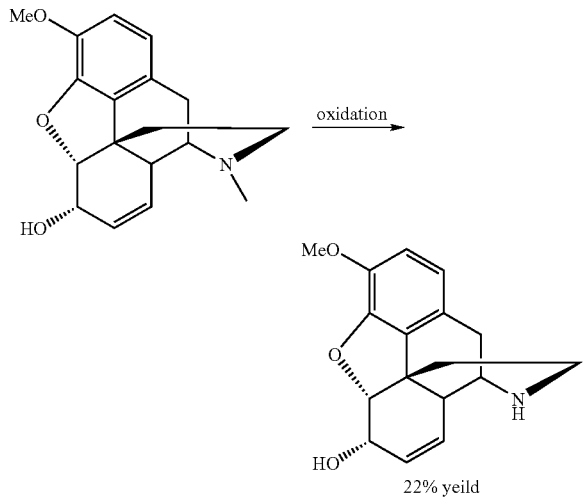

22% yeild

All analytical data for compounds are in agreement with that reported in the literature.

One or more currently preferred embodiments have been described by way of example. It will be apparent to persons skilled in the art that a number of variations and modifications can be made without departing from the scope of the invention as defined in the claims.

References:
1. Hageman, H. A. *Org. React* 1953, 7, 198.
2. Von Braun, J. *Chem. Ber.* 1900, 33, 1438.
3. Yu, H.; Prisinzano, T.; Dersch, C. M.; Marcus, J.; Rothman, R. B.; Jacobsen, A. E.; Rice, K. C. *Bioorg. Med. Chem. Lett.* 2002, 12, 165.
4. Cooley, J. H.; Evain, E. J. *Synthesis* 1989, 1.
5. Hobson, J. D.; McCluskey, J. G. *J. Chem. Soc.* 1967, 2015.
6. Montzka, T. A.; Matiskella, J. D.; Partyka, R. A. *Tetrahedron Lett.* 1974, 15, 1325.
7. Rice, K. C. *J. Org. Chem.* 1975, 40, 1850.
8. Olofson, R. A.; Schnur, R. C.; Bunes, L.; Pepe, J. P. *Tetrahedron Lett.* 1977, 1567.
9. Kapnang, H.; Charles, G. *Tetrahedron Lett.* 1983, 24, 3233.
10. Olofson, R. A.; Martz, J. T.; Senet, J.-P.; Piteau, M.; Malfroot, T. *J. Org. Chem.* 1984, 49, 2081.
11. Greiner, E.; Spetea, M.; Krassnig, R.; Schüllner, F.; Aceto, M.; Harris, L. S.; Traynor, J. R.; Woods, J. H.; Coop, A.; Schmidhammer, H. *J. Med. Chem.* 2003, 46, 1758.
12. Hamilton, G. L.; Backes, B. J. *Tetrahedron Lett.* 2006, 47, 2229.
13. Ripper, J. A.; Tiekink, E. R. T.; Scammells, P. *J. Bioorg. Med. Chem. Lett* 2001, 11, 443.
14. Scammells, Peter; Gathergood, Nickolas; Ripper, Justin. Method for demethylation of N-methylmorphinans. PCT Int. Appl. (2002), 25 pp. CODEN: PIXXD2 WO 2002016367 A1 20020228 CAN 136:200331 AN 2002: 157778 CAPLUS.
15. McCamley, Kristy; Ripper, Justin A.; Singer, Robert D.; Scammells, Peter J. Efficient N-Demethylation of Opiate Alkaloids Using a Modified Nonclassical Polonovski Reaction. Journal of Organic Chemistry (2003), 68(25), 9847-9850. CODEN: JOCEAH ISSN: 0022-3263. CAN 140:77288 AN 2003:887142 CAPLUS.
16. Chaudhuri, N. K., Servando, O., Markus, B., Galynkar, I., Sung, M-S., J. Indian Chem. Soc., 62, (1985) 899-903.

What is claimed is:

1. A one pot single phase method for the N-demethylation of an N-methylated heterocycle comprising mixing the N-methylated heterocycle with a metal catalyst in the presence of an oxidizing agent, wherein the N-methylated heterocycle is selected from the group consisting of a morphine alkaloid and derivatives thereof.

2. A method according to claim 1 wherein the metal catalyst and the oxidizing agent are the same.

3. A method according to claim 1 wherein the oxidizing agent is selected from the group consisting of oxygen, ammonium persulfate, hydrogen peroxide, m-CPBA, peracetic acid, magnesium mono peroxyphthalate; palladium, palladium acetate and combinations thereof.

4. A method according to claim 3 wherein the oxidizing agent is oxygen.

5. A method according to claim 3 wherein the oxidizing agent is palladium acetate.

6. The method according to claim 3 wherein the oxidizing agent is ammonium persulfate.

7. A method according to claim 1 wherein the catalyst is selected from the group consisting of: CuCl, CuI, CuOAc$_2$, CuCO$_3$, CuSO$_4$, CuCl$_2$, CuO, Pd(OAc)$_2$, PdCl$_2$, PdCl$_2$ (PPh$_3$)$_4$, PdBr$_2$, Pd(acac)$_2$, Pd$_2$(dba)$_3$, Pd(dba)$_2$, Pd(PPh$_3$)$_4$, Fe dust, Cu, Fe, Ru, Co, Rh, Ir, Ni, Pd, Pt, Ge, Sn, Os, Ag, Au, and Pb.

8. A method according to claim 7 wherein the catalyst is selected from the group consisting of: Os, Ag, Au, and Pb.

9. A method according to claim 7 wherein the catalyst is selected from the group consisting of: Cu, Fe, Ru, Co, Rh, Ir, Ni, Pd, Pt, Ge, and Sn.

10. A method according to claim 7 wherein the catalyst is selected from the group consisting of: CuCl, CuI, CuOAc$_2$, CuCO$_3$, CuSO$_4$, CuCl$_2$, CuO, Pd(OAc)$_2$, PdCl$_2$, PdCl$_2$(PPh$_3$)$_4$, PdBr$_2$, Pd(acac)$_2$, Pd2(dba)$_3$, Pd(dba)$_2$, Pd(PPh$_3$)$_4$, and Fe dust.

11. The method according to claim 1, wherein the catalyst is a palladium catalyst.

12. The method according to claim 11, wherein the catalyst is selected from the group consisting of PdCl$_2$, Pd(OAc)$_2$, Pd(PPh$_3$)$_4$, Pd$_2$(dba)$_3$ and Pd(dba)$_2$.

13. The method according to claim 11, wherein the catalyst is Pd(OAc)$_2$.

14. The method according to claim 7, wherein the metal catalyst is a copper catalyst.

15. The method according to claim 14, wherein the catalyst is selected from the group consisting of Cu, CuCl, CuI, Cu(OAc)$_2$, CuCO$_3$, CuSO$_4$, CuCl$_2$, and CuO.

16. The method according to claim 15, wherein the catalyst is Cu(OAc)$_2$.

17. The method according to claim 1, wherein the catalyst is present in the range of from about 0.1 equivalents to about 5.0 equivalents.

18. The method according to claim 17, wherein the catalyst is present in the range of from about 1.0 equivalents to 2.5 equivalents.

19. The method according to claim 18, wherein the catalyst is present in about 2.5 equivalents.

20. The method according to claim 1, wherein the catalyst is present in the range of from about 0.1 equivalents to 5.0 equivalents and the oxidizing agent is present in the range of about 1.0 equivalents to 8.0 equivalents.

21. The method according to claim 20, wherein the catalyst is present in the range of from about 1.0 equivalents to 2.5 equivalents and the oxidizing agent is present in the range of 2.0 equivalents to 4.0 equivalents.

22. The method according to claim 21, wherein the catalyst is a copper salt and the oxidizing agent is ammonium persulfate.

23. The method according to claim 22, wherein the copper salt is present in about 2.0 equivalents and the ammonium persulfate is present in 4.0 equivalents.

24. The method according to claim 1, wherein the N-methylated heterocycle is a morphine alkaloid.

25. The method according to claim 24, wherein the morphine alkaloid is selected from the group below: thebaine, oripavine, 14-hydroxycodeinone, 14-hydroxymorphinone, morphine, codeine, hydromorphone, hydrocodone, oxymorphone, oxycodone, hydromorphol and oxymorphol.

26. The method according to claim 25, wherein the morphine alkaloid is hydrocodone.

27. The method according to claim 1, further comprising the addition of at least one solvent wherein said solvent is selected from the group consisting of water, benzene, dioxane, toluene, acetonitrile, C1 to C4 alcohols and mixtures thereof.

28. The method according to claim 27, wherein the at least one solvent is dioxane.

29. The method according to claim 27, wherein the at least one solvent is acetonitrile.

30. The method according to claim 27, wherein the solvent comprises acetonitrile and water.

31. The method according to claim 30, wherein the acetonitrile and water are present in a ratio of about 10:0.5.

32. The method of claim 31 wherein the solvent comprises an acetonitrile: water ratio of about 5:1.

\* \* \* \* \*

UNITED STATES PATENT AND TRADEMARK OFFICE
CERTIFICATE OF CORRECTION

| | |
|---|---|
| PATENT NO. | : 7,935,820 B2 |
| APPLICATION NO. | : 11/771227 |
| DATED | : May 3, 2011 |
| INVENTOR(S) | : Robert James Carroll et al. |

It is certified that error appears in the above-identified patent and that said Letters Patent is hereby corrected as shown below:

In the Claims

Claim 3, Column 8, line 57, "peroxyphthalate;" should read --peroxyphthalate,--.
Claim 7, Column 8, line 66, "CuOAc$_2$" should read --Cu(OAc)$_2$--.
Claim 10, Column 9, line 10, "CuOAc$_2$" should read --Cu(OAc)$_2$--.
Claim 10, Column 9, line 12, "Pd2(dba)$_3$" should read --Pd$_2$(dba)$_3$--.

Signed and Sealed this
Thirtieth Day of July, 2013

Teresa Stanek Rea
*Acting Director of the United States Patent and Trademark Office*